(12) United States Patent
Temple

(10) Patent No.: US 7,905,858 B2
(45) Date of Patent: Mar. 15, 2011

(54) SYSTEM AND METHOD FOR PROVIDING WARM, PRESSURIZED IRRIGATION FLUID

(76) Inventor: John Temple, Chelsea, MI (US)

( * ) Notice: Subject to any disclaimer, the term of this patent is extended or adjusted under 35 U.S.C. 154(b) by 93 days.

(21) Appl. No.: 12/048,466

(22) Filed: Mar. 14, 2008

(65) Prior Publication Data
US 2009/0234287 A1    Sep. 17, 2009

(51) Int. Cl.
*A61F 7/12* (2006.01)
*A61M 37/00* (2006.01)
*A61B 19/00* (2006.01)

(52) U.S. Cl. ......... 604/113; 604/141; 604/142; 604/408

(58) Field of Classification Search ................ 604/113, 604/142, 253, 408, 132, 141
See application file for complete search history.

(56) References Cited

U.S. PATENT DOCUMENTS

| | | | | |
|---|---|---|---|---|
| 4,090,514 A * | 5/1978 | Hinck et al. | ................... | 604/142 |
| 4,106,499 A * | 8/1978 | Ueda | .............................. | 600/499 |
| 5,263,929 A * | 11/1993 | Falcone et al. | ................... | 604/89 |
| 5,295,964 A * | 3/1994 | Gauthier | ........................ | 604/113 |
| 5,733,263 A | 3/1998 | Wheatman | | |
| 6,824,528 B1 | 11/2004 | Faries, Jr. et al. | | |
| 2003/0163087 A1* | 8/2003 | Noice et al. | ................... | 604/113 |
| 2008/0065229 A1* | 3/2008 | Adams | ........................ | 623/23.75 |

* cited by examiner

*Primary Examiner* — Nicholas D Lucchesi
*Assistant Examiner* — Brooke M Matney
(74) *Attorney, Agent, or Firm* — Gifford, Krass, Sprinkle, Anderson & Citkowski, P.C.

(57) ABSTRACT

An economical yet effective apparatus and associated method heats and pressurizes a fluid-filled bag of the type used in a surgical setting. The apparatus includes an inner sealed flexible jacket including a sodium acetate solution and activator button therein operative to heat the fluid-filled bag. An outer sealed flexible jacket adjacent to the inner jacket includes a gas inlet for inflation thereof thereby applying pressure to the fluid-filled bag through the heated inner jacket during use.

12 Claims, 8 Drawing Sheets

SYSTEM AND METHOD FOR PROVIDING WARM, PRESSURIZED IRRIGATION FLUID

FIELD OF THE INVENTION

This invention relates generally to surgical irrigation and, in particular, to an economical yet effective apparatus and associated method for heating and pressurizing a fluid-filled bag.

BACKGROUND OF THE INVENTION

During surgical procedures it is advantageous to provide warm, pressurized fluids for irrigation and infusion. According to U.S. Pat. No. 5,733,263, an apparatus is provided for heating fluid contained in one or more bags and delivering the fluid from at least one bag to a surgical patient. The apparatus includes a housing sized and shaped to enclose at least one bag containing fluid and having a door positioned to provide access to an interior of the housing. The apparatus also includes an inflatable bladder mounted in the interior of the housing and connected to a source of pressurized fluid for inflation. The inflatable bladder is positioned within the housing for exerting force against at least one bag mounted within the housing. The apparatus also includes a heater mounted adjacent the housing door in heat transfer relationship with the fluid in at least one bag. The invention also provides a method for maintaining the temperature of fluid contained in one or more bags and for delivering the fluid from at least one bag to a surgical patient.

A simpler system is described in U.S. Pat. No. 6,824,528. A method and apparatus for pressure infusion and temperature control of infused liquids includes a receptacle for receiving a liquid-filled bag containing intravenous solution or other liquid and an inflatable pressure device. The inflatable pressure device is disposed within a pressure device bag and is positioned proximate the liquid-filled bag in the receptacle. The inflatable pressure device expands within the pressure device bag upon inflation and exerts pressure on the liquid-filled bag. A heating element may be disposed on the inflatable pressure device bag to heat the liquid-filled bag to a desired temperature. The liquid may alternatively be maintained at a desired temperature, while flowing to a patient via a heating assembly disposed along a tube. The heating assembly includes a sleeve having a slot for receiving the tube and a plurality of individually controlled heaters. An infrared sensing device is mounted proximate a drip chamber to ascertain a drip count, while a temperature sensor is disposed within a holder that is positioned toward the entry site on a patient. A heat controller controls the heaters based on a drip count, while a safety controller disables heater operation in response to liquid temperature exceeding the desired temperature. Alternatively, the liquid-filled bag may be heated to a desired temperature whereby the heating assembly includes a single heater controlled by a controller to maintain the liquid at the desired temperature during infusion of the liquid into a patient.

While systems do exist for providing heated, pressurized fluids for surgical purposes, they tend to be overcomplicated and not very cost effective.

SUMMARY OF THE INVENTION

This invention resides in an economical yet effective apparatus and associated method for heating and pressurizing a fluid-filled bag of the type used in a surgical setting. The apparatus broadly includes an inner sealed flexible jacket sized to encase the bag, the inner jacket including a sodium acetate solution and activator button therein operative to heat the fluid-filled bag during use. An outer sealed flexible jacket adjacent to the inner jacket includes a gas inlet for inflation thereof, thereby applying pressure to the fluid-filled bag through the inner jacket.

The inner jacket may include sealed partitions to maintain a desired thickness, and the first and second jackets may be coextensive and peripherally joined. In the preferred embodiment, the apparatus is formed into a cylindrical sleeve to receive the fluid-filled bag with bottom straps to prevent the bag from falling out.

In an alternative embodiment the jackets are wrapped around the fluid-filled bag. In this configuration, a first side edge of the assembly includes a bent metal wire forming an elongate slot. A second, opposing side edge includes a flap extending therefrom, the flap terminating in a first elongate strip of hoop-and-loop fastener material. A second elongate strip of hoop-and-loop fastener material is disposed on the outer surface of the outer jacket, enabling the flap to be inserted through the slot and folded back over so that the first and second elongate strips of hoop-and-loop fastener material connect and maintain the jackets in wrapped position around the fluid-filled bag.

DETAILED DESCRIPTION OF THE INVENTION

Figure 1:
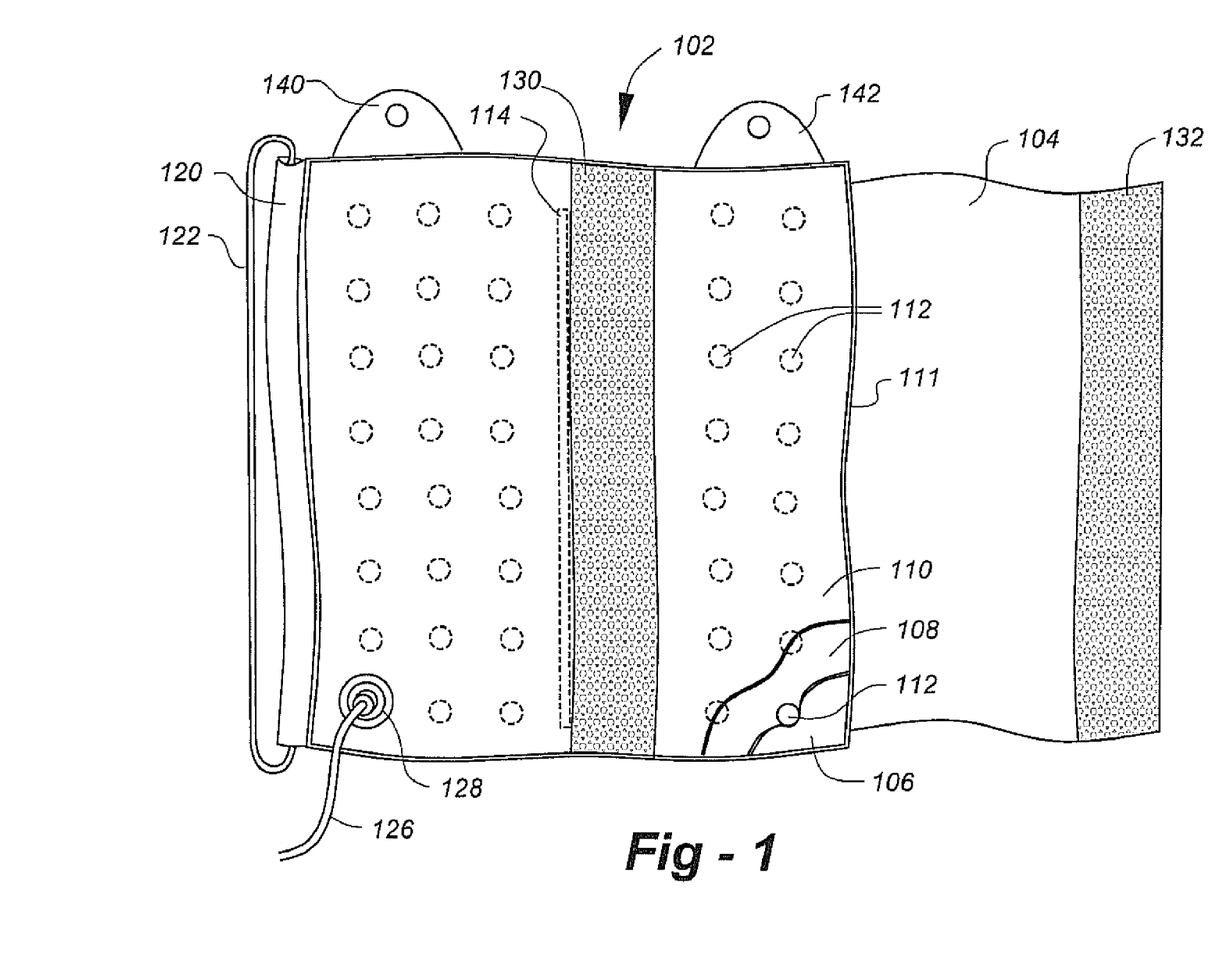
FIG. 1 is a drawing of an embodiment of the invention in an unwrapped state seen from the outermost layer.

FIG. 1 is a drawing which shows an embodiment of the invention indicated generally at 102. The system includes three layers of flexible material, which are peripherally joined to create two sealed pads. In this embodiment, layers 106, 108, 110 are co-extensive, enabling a single peripheral seal 111 to be used to join all three layers. This creates two co-extensive liquid- and gas-impermeable pads, namely, a pad between layers 106 and 108, and a separate pad between layers 108 and 110.

Figure 2:
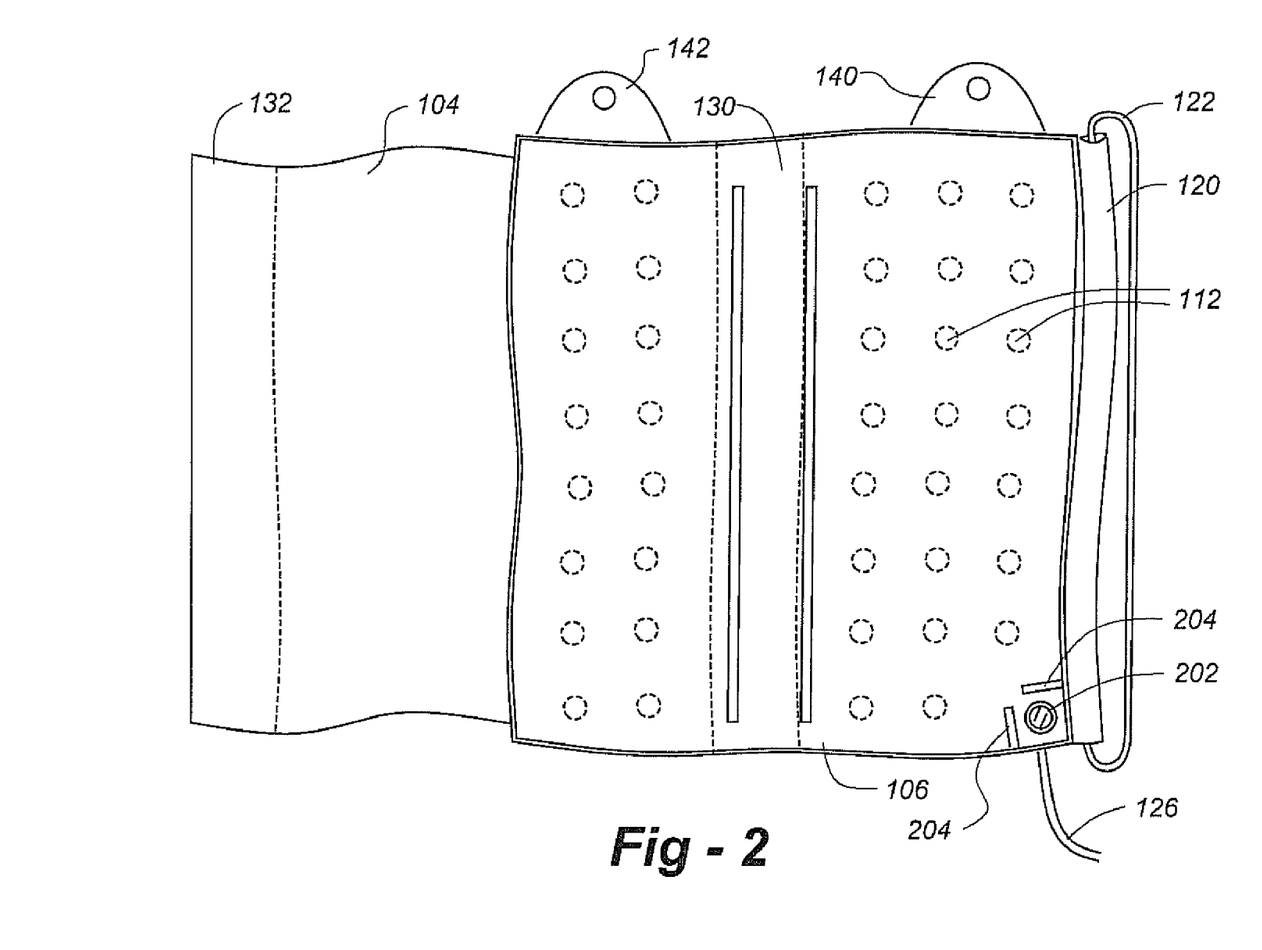
FIG. 2 is a drawing of an embodiment of the invention in an unwrapped state seen from the innermost layer.

The pad between layers 106 and 108 is filled with sodium acetate solution, and an activator button 202, best seen in FIG. 2, is used to activate the solution, causing it to rise to the temperature on the order of 135° F. The pad formed between layers 108 and 110, is inflated through conduit 126, joined to the outermost layer through connector 128. Conduit 126 is inflated from an available $CO_2$ or other gas supply though, in alternative embodiments, an acid/base mixture or a manually operated bulb may instead be used as described in further detail below.

On one side edge of the assembly 102, there is a flap 104 including the first portion of a hook-and-loop fastener material 132 at its distal end. A second strip of hook-and-loop material 130 is disposed on the outermost surface 110. At the other opposing side edge of the assembly 102, a bent wire 122 is entrapped by slot 120, creating an elongate slot in which flap 104 is inserted and folded back onto the assembly, as described in further detail below. Portions of the pad created between layers 106 and 108 may be thermally joined into dots 112 and/or elongate lines 114. This allows the pad created between layers 106 and 108 to have a relatively consistent thickness, while at the time, allowing fluid flow in and around the various thermal wells. Elongate lines 114 assist with folding around a irrigation fluid bag, as further described below. Tabs 140, 142 facilitate hanging, as also described below.

FIG. 2 is a drawing seen from the innermost layer, wherein like numerals refer to the same structures introduced with respect to FIG. 1. More visible in FIG. 2, however, is an activator disk 202, which may be partitioned from the main volume of the pad created between layers 106, 108 using thermally welded partitions 204. In operation, once the assembly 102 is wrapped around the bag of irritation fluid, the activator disk 202 is clicked, causing a catalytic reaction causing the sodium acetate to release heat.

Figure 3:
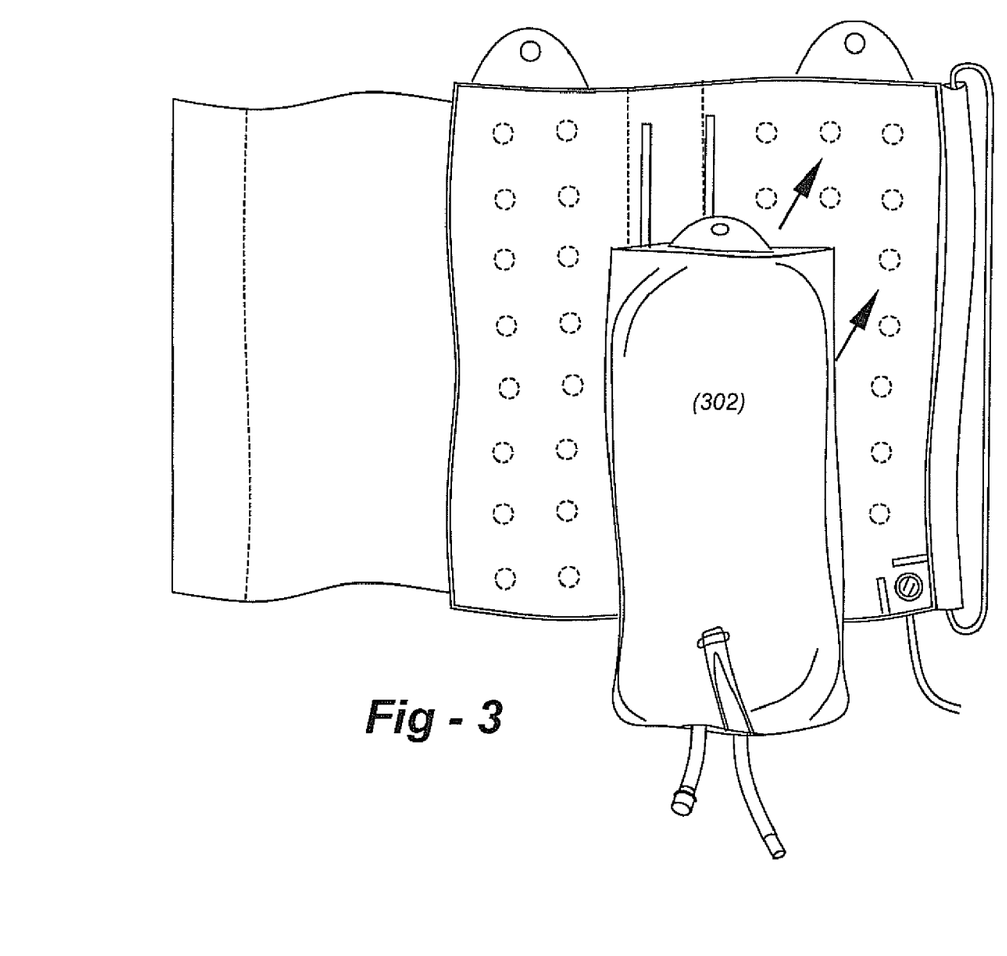
FIG. 3 is a drawing which shows how a bag filled with irrigation fluid is placed onto the innermost layer.
Figure 4:
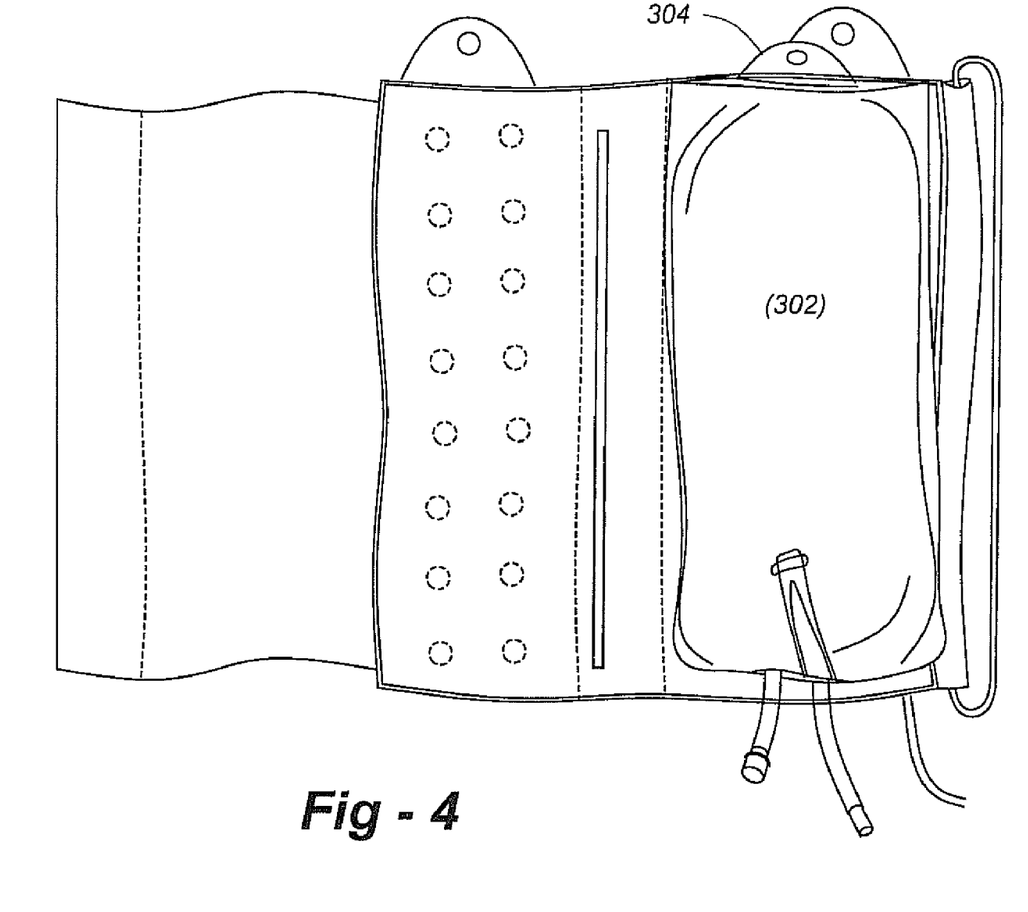
FIG. 4 is a drawing which shows a continuation of FIG. 3, with the irrigation fluid bag more aligned.

FIG. 3 is a drawing which shows how a bag of irrigation fluid 302 is placed onto the innermost surface of the assembly, and FIG. 4 shows how the bag is preferably finally aligned, such that tab 304 on bag 302 is generally overlapping with tab 140 on the assembly 102.

Figure 5:
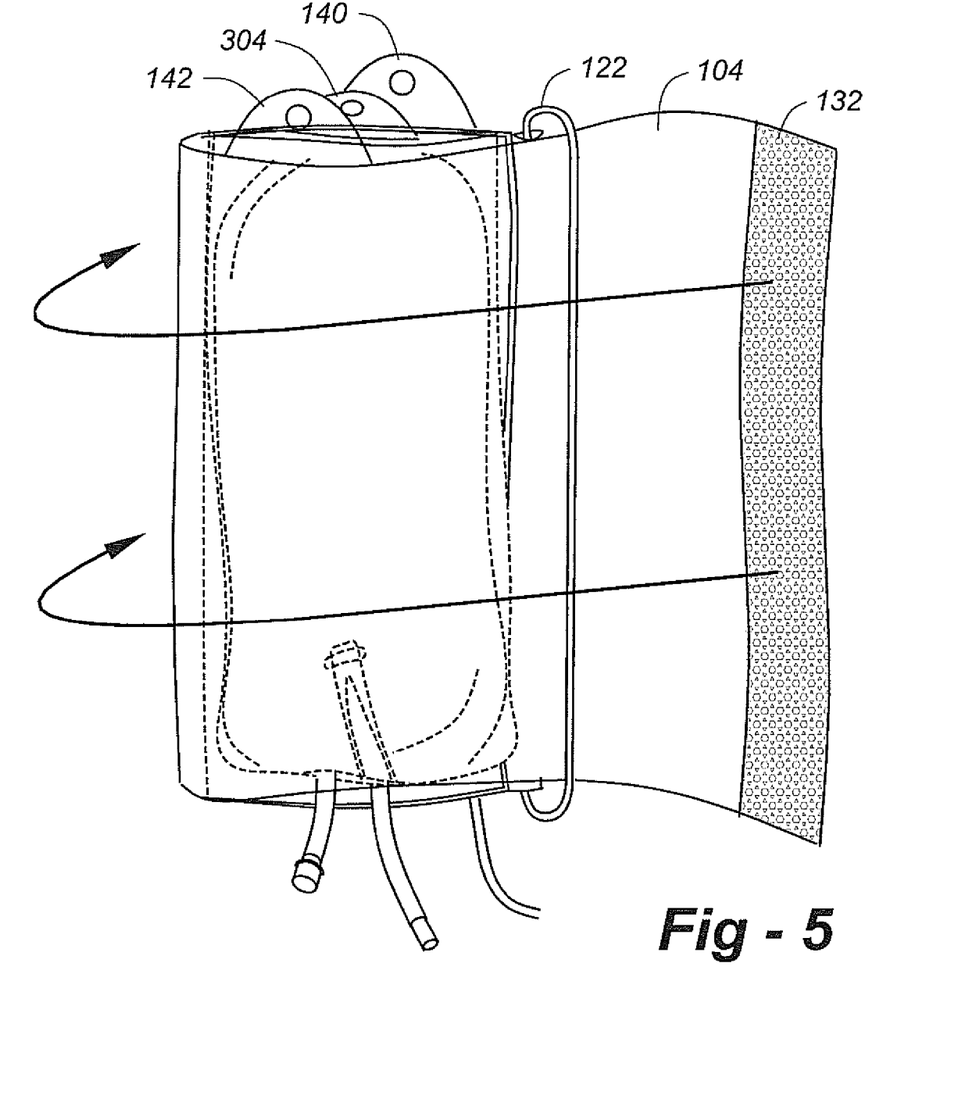
FIG. 5 is a drawing which shows a next stage in conjunction with wrapping the bag of irrigation fluid, with a flap dressed through and elongate slot prior to closure.
Figures 6, 7:
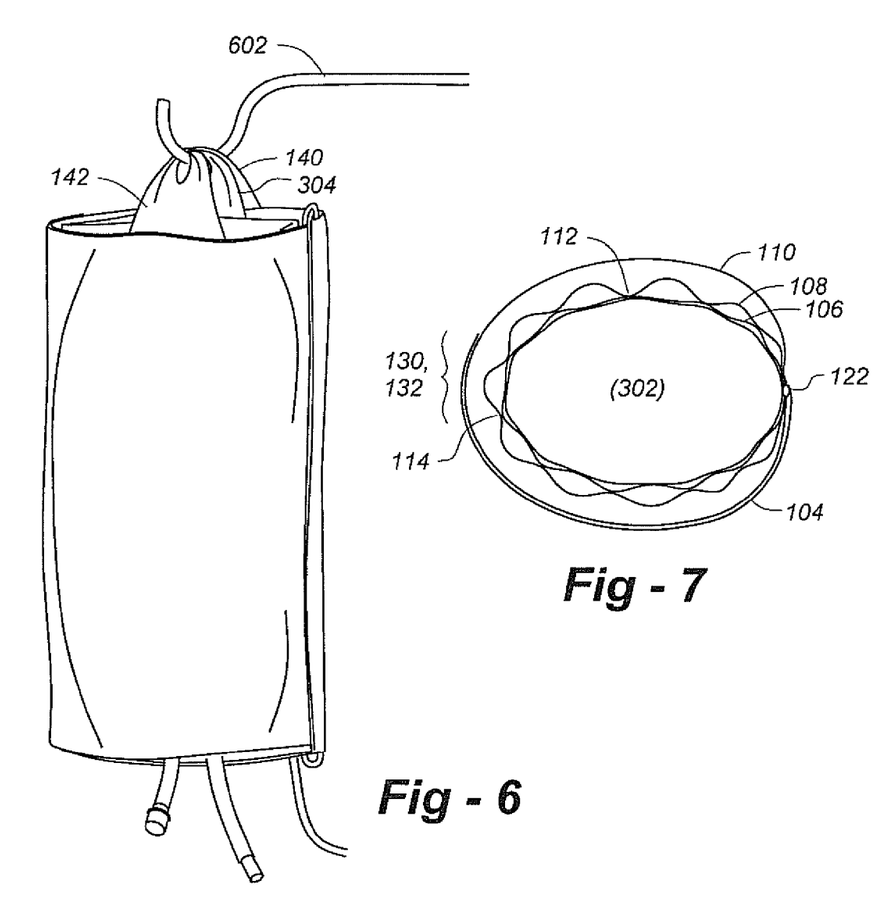
FIG. 6 is a drawing showing the invention entirely wrapped around a bag of irrigation fluid, both being hung on a hook for use.
FIG. 7 is a cross-section of the invention encasing a bag of irrigation fluid.

FIG. 5 shows a continuation of the method of the invention, wherein flap 104 is dressed through bent wire 122, and wrapped around until the two hook-and-loop fastener strips are joined. Although bent wire 122 is used in the preferred embodiment, an elongate slot may be created in other ways, including the use of a strip of rigid plastic, or the like. As shown in FIG. 6, once the assembly is wrapped around the bag of irrigation fluid, the three tabs are aligned so that they may be placed over hooks 602 as is common in surgical settings. At this time, the activator disk in the sodium acetate solution is activated, and the outer jacket is pressurized, applying both heat and temperature to the bag of irrigation fluid. Conveniently, the use of a pressurization jacket outside of an inner warming jacket provides an additional layer of insulation, thereby maintaining temperature of the irrigation fluid for a longer period of time.

FIG. 7 is a cross-section of the assembly, taken through points and lines of thermal welding 112, 114. In terms of materials, polyvinyl chloride PVC) is used for the three layers 106, 108, 110, though other gas- and liquid-impermeable materials may alternatively be used. In the preferred embodiment, the assembly is provided in a non-sterilized form, and is discarded after use, owing it its relatively low price.

Figure 8:
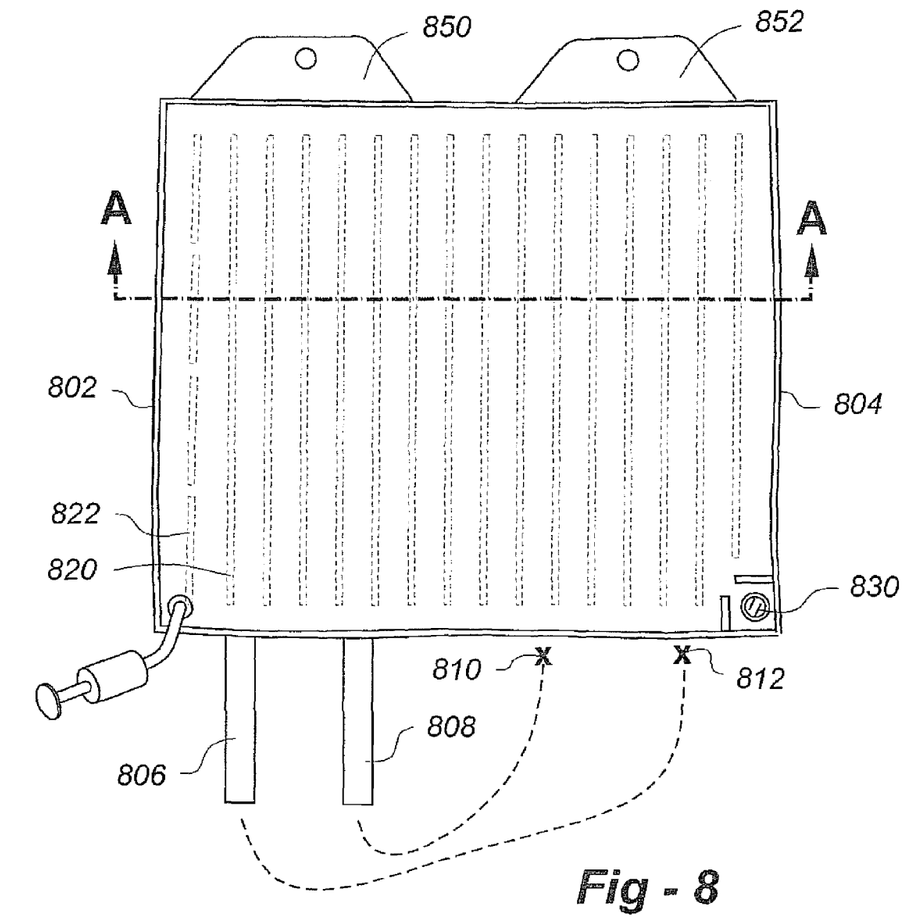
FIG. 8 is a drawing of a preferred embodiment of the invention prior to complete assembly.
Figure 11:
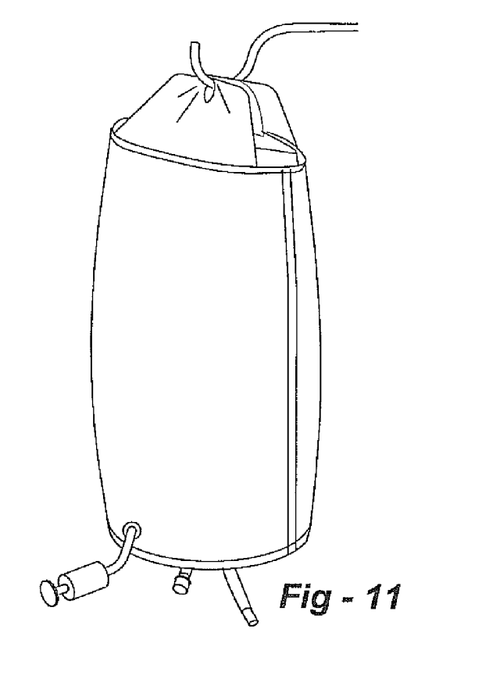
FIG. 11 shows the invention and fluid-filled bag in a banging configuration.
Figure 12:
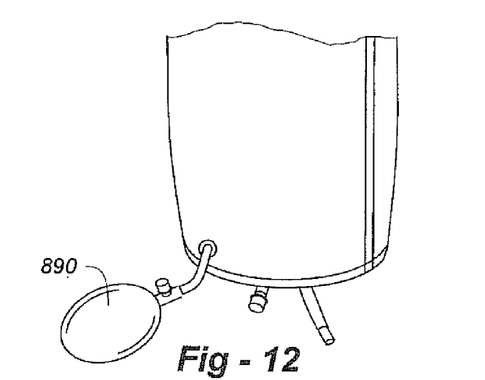
FIG. 12 illustrates an alternate inflation mechanism in the form of a bulb-type hand pump.

FIG. 8 is a drawing of a preferred embodiment of the invention prior to complete assembly. Since the outer dimensions of common fluid-filled hospital bags is known in advance, this embodiment uses a preformed sleeve into which the fluid-filled bag is dropped into as opposed to a wrapping process. In FIG. 8, edges 802 and 804 will be joined for final assembly, and straps 806, 808 will we joined at points 801, 812 to keep the fluid-filled bag from falling out of the bottom as shown in FIGS. 11 and 12. Optional sealed partitions may be provided, which may be continuous (820) or broken (822). The activator disc is show at 830.

Figure 9:
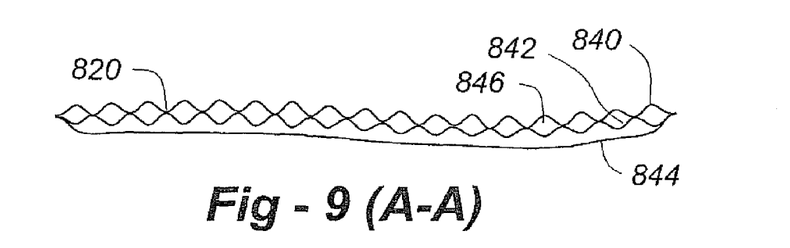
FIG. 9 is a cross-section of the embodiment of FIG. 8.

FIG. 9 is a cross-section of the embodiment of FIG. 8 taken along line A-A. Three sheets of material 840, 842 and 844 are used to create an inner sealed jacket 846 that will be heated through sodium acetate activation and an outer sealed jacket 848 which will be inflated. In the preferred embodiment, layer 842 provides a common wall between the inner and outer jackets. Tabs 850, 852 will oppose one another when the device is assembled. The same materials may be used in any of the embodiments described herein.

Figure 10:
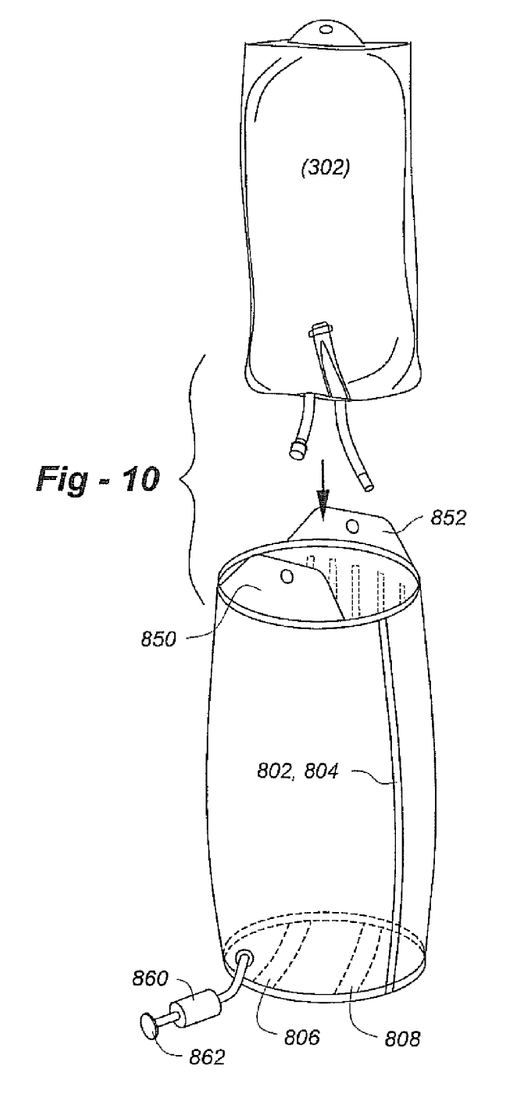
FIG. 10 shows a fluid-filled bag being inserted into a completed version of the preferred embodiment.

FIG. 10 shows a fluid-filled bag being inserted into a completed version of the preferred embodiment. Also shown is a device 860 containing acetic acid and sodium bicarbonate which are mixed through action of plunger 862, thereby inflating the outer jacket. Other acid/base or gas-releasing chemicals may alternatively be used. As a further alternative, the manually operated bulb 890 shown in FIG. 12 may be used in this or any other of the embodiments disclosed herein. FIG. 11 shows the invention and fluid-filled bag in a hanging configuration ready for use.

I claim:

1. Apparatus for heating and pressurizing a fluid-filled bag, comprising:
    a flexible, tubular sleeve configured to receive a fluid-filled bag having an outer wall;
    the flexible, tubular sleeve including substantially co-extensive inner and outer sealed jackets, both configured to wrap entirely around the outer wall of the fluid-filled bag;
    the inner sealed jacket being filled with a sodium acetate solution and including an activator button operative to initiate an exothermic reaction within the solution, causing the inner jacket to become heated;
    a substance or device for inflating the outer sealed jacket, thereby applying pressure and heat to the entire outer wall of the fluid-filled bag through the heated inner jacket.

2. The apparatus of claim 1, wherein the substance or device for inflating the outer sealed jacket includes:
    a container including acetic acid and sodium bicarbonate in communication with the outer sealed jacket; and
    a manually operable device for mixing the acetic acid and sodium bicarbonate to inflate the outer sealed jacket with carbon dioxide.

3. The apparatus of claim 1, wherein the substance or device for inflating the outer sealed jacket includes a manually operated air pump in communication with the outer sealed jacket.

4. The apparatus of claim 1, wherein the substance or device for inflating the outer sealed jacket includes a coupling for connecting the outer sealed jacket to a source of pressurization.

5. The apparatus of claim 1, wherein the inner and outer sealed jackets are substantially coextensive and peripherally bonded to one another.

6. The apparatus of claim 1, wherein the inner and outer sealed jackets share a common wall.

7. The apparatus of claim 1, wherein the inner jacket includes heat-sealed regions to maintain a desired thickness.

8. The apparatus of claim 1, further including one or more hanging tabs.

9. The apparatus of claim 1, wherein the inner and outer jackets are constructed of polyvinyl chloride (PVC) or other thermoplastic rubber sheets.

10. The apparatus of claim 1, further including a set of hook-and-loop fasteners for maintaining the jackets in a wrapped position around the fluid-filled bag.

11. The apparatus of claim 1, further including:
a first side edge with an elongate slot;
a second, opposing side edge with a flap extending therefrom, the flap terminating in a first elongate strip of hoop-and-loop fastener material; and
a second elongate strip of hoop-and-loop fastener material disposed on the outer surface of the outer jacket, enabling the flap to be inserted through the slot and folded back over so that the first and second elongate strips of hoop-and-loop fastener material connect and maintain the jackets in wrapped position around the fluid-filled bag.

12. The apparatus of claim 1, further including:
a first side edge with a bent metal wire forming an elongate slot;
a second, opposing side edge with a flap extending therefrom, the flap terminating in a first elongate strip of hoop-and-loop fastener material; and
a second elongate strip of hoop-and-loop fastener material disposed on the outer surface of the outer jacket, enabling the flap to be inserted through the slot and folded back over so that the first and second elongate strips of hoop-and-loop fastener material connect and maintain the jackets in wrapped position around the fluid-filled bag.

* * * * *